(12) United States Patent
Kraemer

(10) Patent No.: US 10,076,364 B2
(45) Date of Patent: Sep. 18, 2018

(54) MINIMAL-PROFILE ANTERIOR CERVICAL PLATE AND CAGE APPARATUS AND METHOD OF USING SAME

(71) Applicant: K2M, Inc., Leesburg, VA (US)

(72) Inventor: Paul Edward Kraemer, Westfield, IN (US)

(73) Assignee: K2M, Inc., Leesburg, VA (US)

( * ) Notice: Subject to any disclaimer, the term of this patent is extended or adjusted under 35 U.S.C. 154(b) by 248 days.

(21) Appl. No.: 13/932,676

(22) Filed: Jul. 1, 2013

(65) Prior Publication Data

US 2014/0005727 A1      Jan. 2, 2014

Related U.S. Application Data

(60) Provisional application No. 61/665,934, filed on Jun. 29, 2012.

(51) Int. Cl.
| | | |
|---|---|---|
| *A61F 2/44* | (2006.01) | |
| *A61B 17/58* | (2006.01) | |
| *A61B 17/70* | (2006.01) | |
| *A61B 17/88* | (2006.01) | |
| *A61B 17/00* | (2006.01) | |
| *A61F 2/30* | (2006.01) | |

(52) U.S. Cl.
CPC .......... *A61B 17/7059* (2013.01); *A61B 17/88* (2013.01); *A61F 2/4455* (2013.01); *A61B 2017/00261* (2013.01); *A61F 2/447* (2013.01); *A61F 2002/30331* (2013.01); *A61F 2002/30383* (2013.01); *A61F 2002/30578* (2013.01)

(58) Field of Classification Search
CPC . A61B 17/8061; A61B 17/80; A61B 17/7059; A61B 17/88; A61F 2002/30517; A61F 2002/30576; A61F 2/4455–2/447
USPC .............. 606/246, 247, 249, 279, 280, 286; 623/17.11, 17.16
See application file for complete search history.

(56) References Cited

U.S. PATENT DOCUMENTS

| | | | | |
|---|---|---|---|---|
| 6,066,175 | A  * | 5/2000 | Henderson | ................ A61F 2/44 623/17.11 |
| 6,113,637 | A  * | 9/2000 | Gill et al. | ................... 623/17.15 |
| 6,364,880 | B1 * | 4/2002 | Michelson | ..................... 606/247 |
| 8,403,970 | B1 * | 3/2013 | Bedor | ........................... 606/289 |
| 8,956,415 | B2 * | 2/2015 | Cowan | ........................ 623/17.16 |
| 9,872,781 | B2 * | 1/2018 | Pavento | .................. A61F 2/447 |
| 2006/0085071 | A1 * | 4/2006 | Lechmann | ............. A61B 17/86 623/17.11 |
| 2007/0123987 | A1 * | 5/2007 | Bernstein | .................. A61F 2/44 623/17.11 |
| 2007/0179504 | A1 * | 8/2007 | Kirschman | ....................... 606/69 |
| 2008/0065070 | A1 * | 3/2008 | Freid et al. | ...................... 606/61 |

(Continued)

*Primary Examiner* — Jacqueline Johanas
*Assistant Examiner* — Tessa Matthews
(74) *Attorney, Agent, or Firm* — Carter, DeLuca, Farrell & Schmidt, LLP

(57) ABSTRACT

An apparatus and method for fusing cervical vertebrae is provided. The apparatus may include a plate configured to be affixed to at least two vertebrae, and at least two screws configured to affix the plate to an anterior surface of the at least two vertebrae, wherein when the plate is affixed to the at least two vertebrae, the plate is configured to be partially disposed in a disc space between the at least two vertebrae, and extend in an anterior direction beyond an anterior surface of the at least two vertebrae.

15 Claims, 16 Drawing Sheets

(56) References Cited

U.S. PATENT DOCUMENTS

| | | | |
|---|---|---|---|
| 2010/0070037 A1* | 3/2010 | Parry | A61B 17/7059 623/17.16 |
| 2010/0286781 A1* | 11/2010 | Bullard | A61B 17/7059 623/17.11 |
| 2011/0040334 A1* | 2/2011 | Kaes et al. | 606/279 |
| 2011/0166658 A1* | 7/2011 | Garber | A61F 2/447 623/17.16 |
| 2011/0288590 A1* | 11/2011 | O'Farrell et al. | 606/264 |
| 2012/0041559 A1* | 2/2012 | Melkent | A61F 2/4455 623/17.11 |
| 2012/0065688 A1* | 3/2012 | Nehls | A61B 17/7059 606/279 |
| 2012/0245690 A1* | 9/2012 | Cowan, Jr. | A61F 2/4465 623/17.16 |
| 2013/0053895 A1* | 2/2013 | Stoll et al. | 606/279 |
| 2013/0282127 A1 | 10/2013 | Gray | |
| 2014/0058446 A1* | 2/2014 | Bernstein | 606/246 |

* cited by examiner

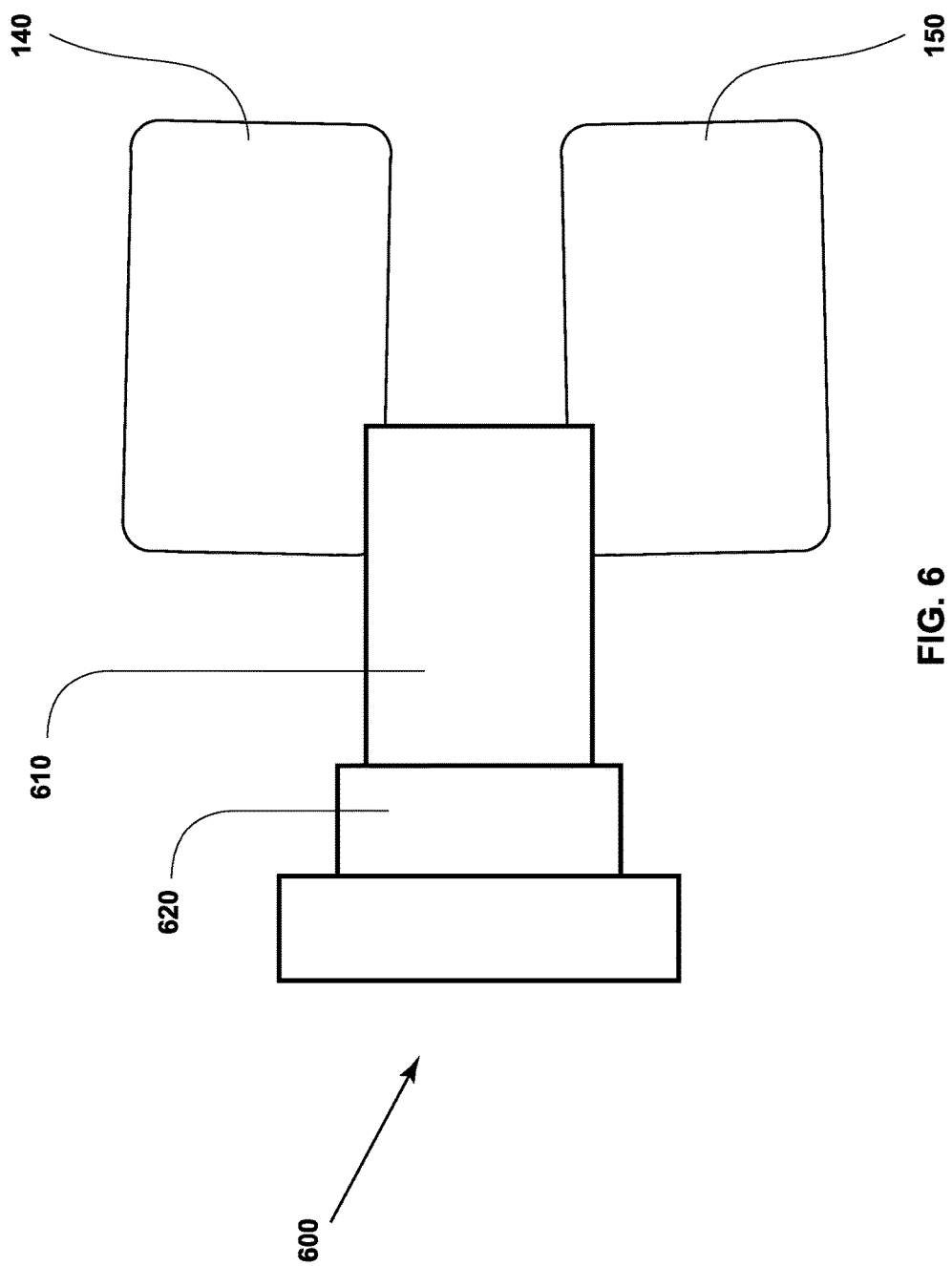

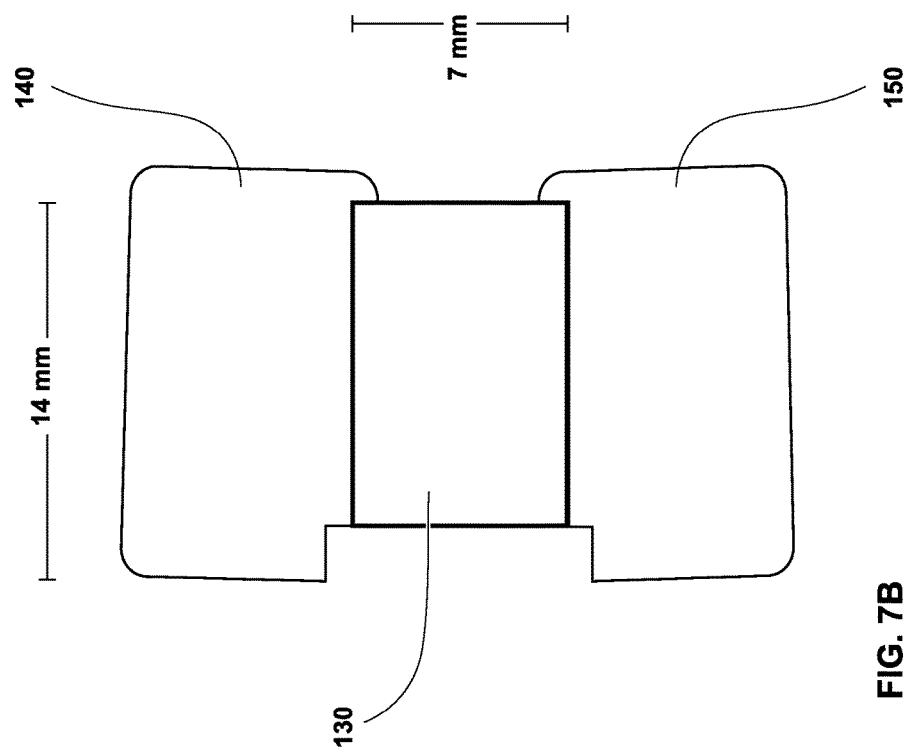
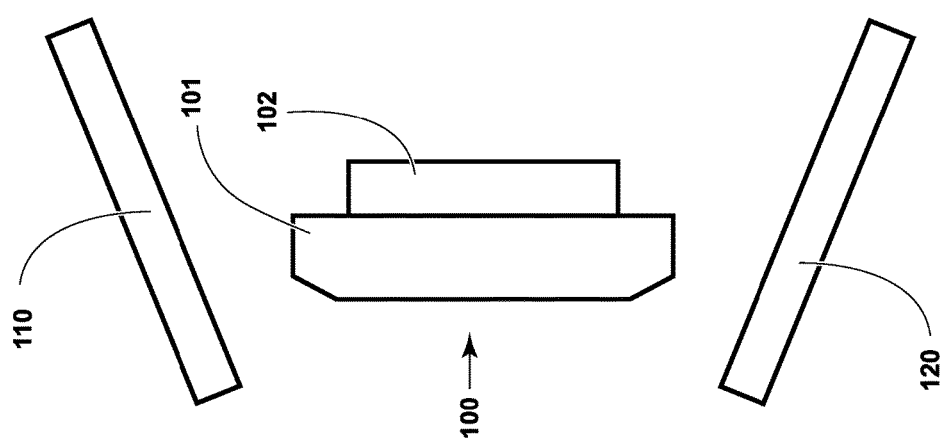
FIG. 7B

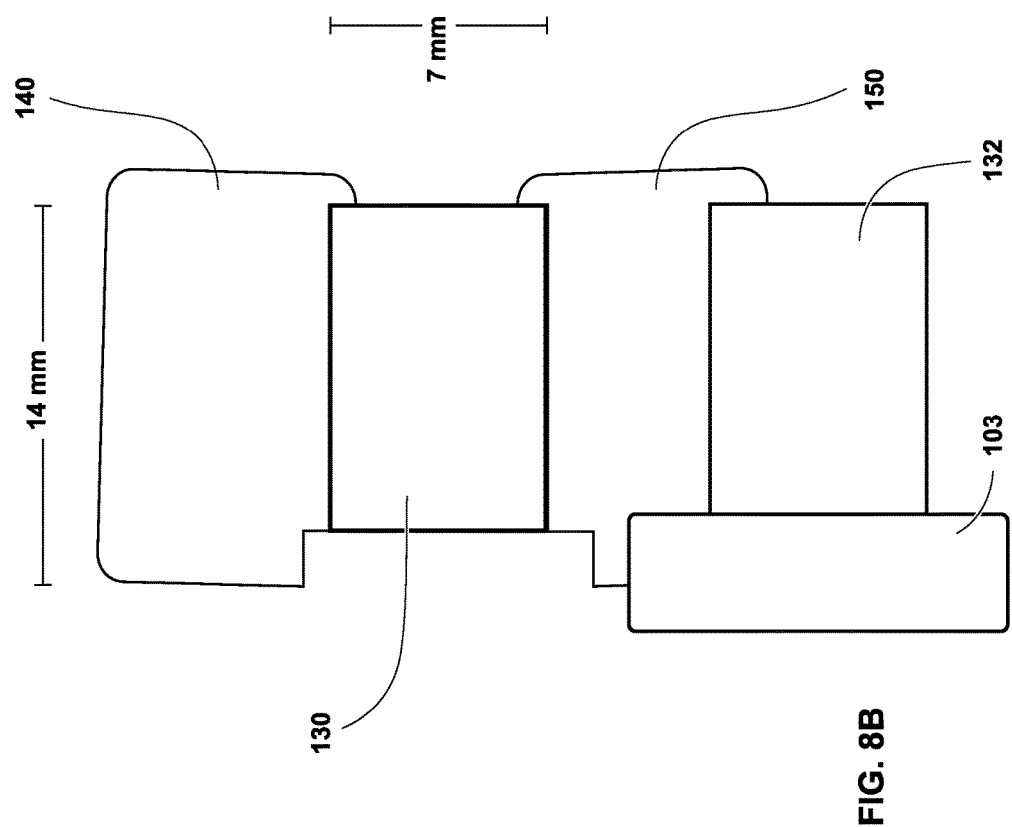
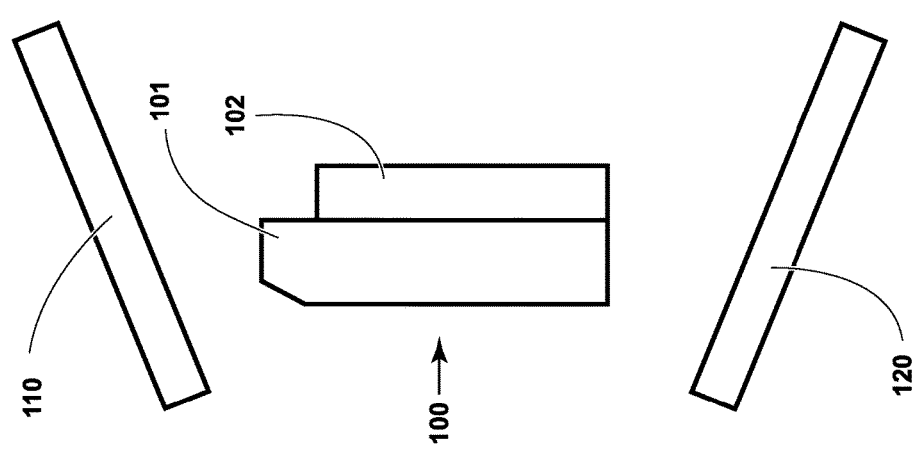
FIG. 8B

MINIMAL-PROFILE ANTERIOR CERVICAL PLATE AND CAGE APPARATUS AND METHOD OF USING SAME

This application claims priority to U.S. Provisional Patent Application No. 61/665,934 filed on Jun. 29, 2012, which is incorporated herein by reference in its entirety.

RELATED ART

Methods and apparatuses consistent with the exemplary embodiments relate to anterior cervical fusion. In particular, the exemplary embodiments relate to an apparatus and method for fusing cervical vertebrae wherein the apparatus secures a graft between vertebrae such that at least a portion of the apparatus extends beyond an anterior face of the vertebrae.

Anterior cervical discectomy and fusion (ACDF) is a procedure commonly used to treat cervical disc herniation. During the procedure, a surgeon removes the herniated disc from in between two vertebrae, and the two vertebrae above and below the disc space are fused together. To facilitate fusion and prevent the vertebrae from collapsing, the open disc space is filled with a bone graft. The bone graft and the vertebrae may be immobilized and held together with a metal plate and screws, which allows the bone graft to eventually join the vertebrae above and below the disc space to form one solid piece of bone. The manner in which the plate and screws are fixed to the vertebrae affect the healing process, and specifically fusing the vertebrae optimally, reproducibly, and with minimal disruption to native tissue.

SUMMARY

Accordingly, there is a need for an improved apparatus and method for facilitating anterior cervical fusion.

According to an aspect of one or more exemplary embodiments, there is provided an apparatus for fusing vertebrae after an anterior cervical discectomy. The apparatus according to one or more exemplary embodiments may include a plate configured to be affixed to an anterior surface of the at least two vertebrae, and at least two screws configured to affix the plate to an anterior surface of the at least two vertebrae. When the plate is affixed to the at least two vertebrae, the plate may extend in an anterior direction beyond the anterior surface of the at least two vertebrae, and may be partially disposed between the at least two vertebrae.

By positioning the plate such that it extends beyond the anterior surface of the two vertebrae, more room is available in the disc space for the bone graft to facilitate fusion. In other words, the surface area of the bone graft is maximized. By contrast, a "zero-profile" apparatus may include a plate that is disposed entirely within the disc space such that the plate does not extend beyond the anterior surface of the vertebrae. Disposing the plate within the disc space reduces the amount of space available for the bone graft, which may hinder vertebrae fusion.

In addition, by partially disposing the plate within the disc space and allowing the plate to extend beyond the anterior surface of the vertebrae, a shorter plate may be used so that a greater distance from the adjacent disc is maintained. If a plate is disposed entirely on the anterior surface of the vertebrae, the plate must be longer in order to accommodate the screws. Using a longer plate, however, reduces the distance between the plate and the adjacent disc, which may be problematic. Thus, by disposing the plate partially within the disc space and partially on the anterior surface of the vertebrae, there is a reduced risk that the plate will negatively affect the adjacent disc. In this configuration the screws may be inserted into the vertebrae at an angle, which is less prone to pullout as compared to horizontal screws.

The plate may extend 3 mm or less in an anterior direction beyond the anterior surface of the at least two vertebrae. The plate and the screws may be disposed such that there is at least 5 mm between the plate and an adjacent disc space.

The apparatus may also include a graft configured to be disposed between the at least two vertebrae. The graft may extend approximately 11 mm to 14 mm in a posterior direction from the anterior surface of the at least two vertebrae. The graft may include structural allograft bone, or a polyether ether ketone (PEEK) cage filled with allograft bone.

The plate may extend approximately 14 mm in a cephalo-caudal direction that is parallel to the anterior surface of the at least two vertebrae. The plate may include an anterior portion that extends in an anterior direction beyond the anterior surface of the at least two vertebrae, and a posterior portion configured to be detachably connected to the anterior portion. The anterior portion of the plate may include two recesses, and the posterior portion may include two anterior protrusions. The two recesses of the anterior portion may receive the two anterior protrusions of the posterior portion. The two anterior protrusions may be hollow, and configured to receive screws for affixing the plate to the vertebrae. The anterior portion may be made of titanium or other metal, and the posterior portion may be made of PEEK or other non-metal substance.

The posterior portion may extend approximately 2 mm in a posterior direction from the anterior surface of the at least two vertebrae, and the graft may extend approximately 12 mm in a posterior direction from the posterior portion of the plate. The posterior portion may extend approximately 10 mm in the cephalo-caudal direction. These dimensions are merely exemplary and one skilled in the art would understand that the dimensions may vary without departing from the inventive concept.

The apparatus may also include a third screw that is configured to fix the plate to the anterior surface of the at least two vertebrae. The third screw may be disposed between the at least two screws.

According to another aspect of one or more exemplary embodiments, there is provided a method for affixing a plate to at least one vertebrate to facilitate fusion after an anterior cervical discectomy. The method according to one or more exemplary embodiments may include carving a channel between the two vertebrae, inserting a graft into the channel, and affixing a plate to the two vertebrae such that a portion of the plate is within the channel and a portion of the plate extends in an anterior direction beyond an anterior surface of the two vertebrae.

The channel may have a posterior portion and an anterior portion. The cephalo-caudal height of the anterior portion may be greater than the cephalo-caudal height of the posterior portion. The posterior depth of the posterior portion may be greater than a posterior depth of the anterior portion. The channel may be carved with a cylindrical burr or router type device. The cylindrical burr may be a two-diameter reamer having a minor diameter channel for the bone graft and a major diameter for the plate. The diameter sizes may be chosen based on the patient's anatomy and/or the size of the plate and graft.

The plate may be affixed to the two vertebrae such that the plate is at least approximately 5 mm from a nearest disc in the cephalad and/or caudal direction.

The graft may extend approximately 11 mm to 14 mm in a posterior direction from the anterior surface of the two vertebrae.

BRIEF DESCRIPTION OF THE DRAWINGS

FIG. 6 is a side view of a reamer that may be used in a method for using fusing two vertebrae according to an exemplary embodiment.

FIGS. 7A-E are exploded views of a fusion apparatus according to an exemplary embodiment as the apparatus is affixed to the vertebrae.

FIGS. 8A-E are exploded views of a fusion apparatus according to another exemplary embodiment as the apparatus is affixed to the vertebrae.

DETAILED DESCRIPTION OF EXEMPLARY EMBODIMENTS

Figure 1:
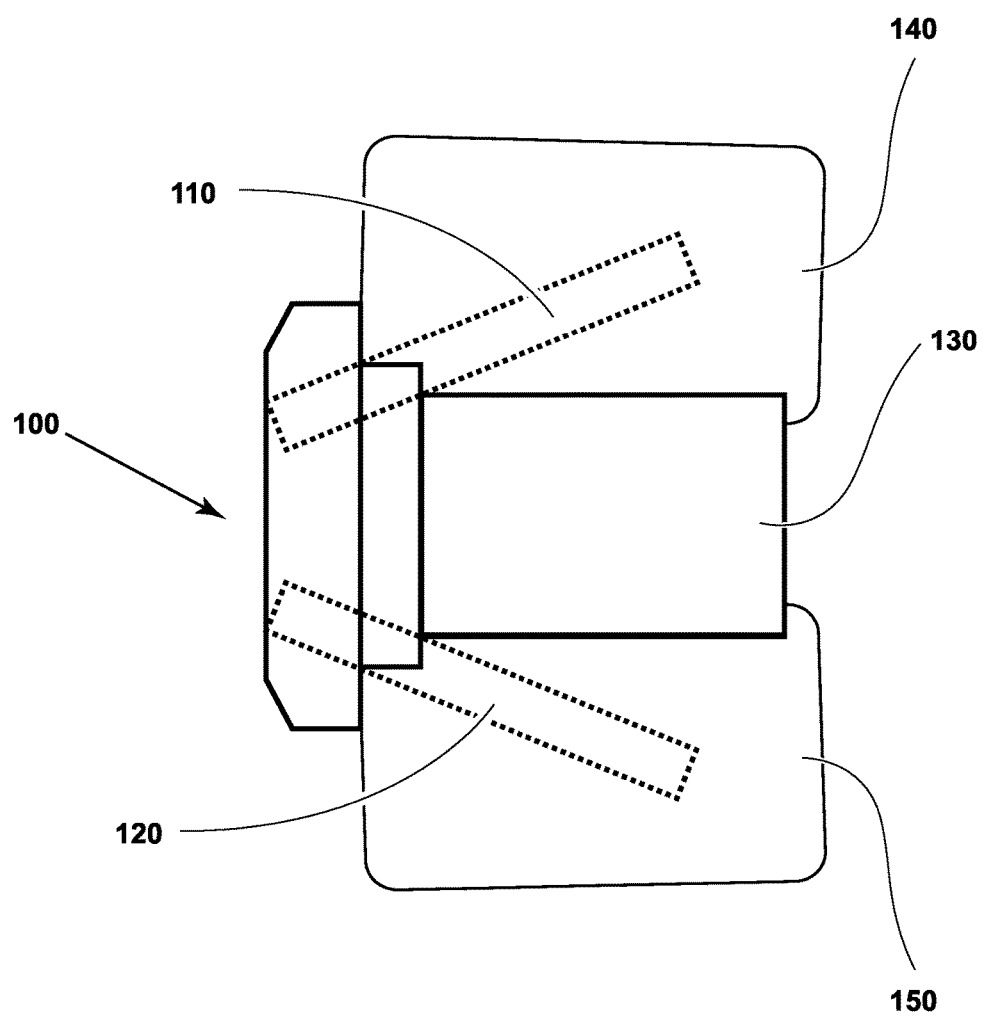
FIG. 1 is a lateral view of a fusion apparatus according an exemplary embodiment.

Reference will now be made in detail to the following exemplary embodiments, which are illustrated in the accompanying drawings, wherein like reference numerals refer to like elements throughout.

The exemplary embodiments may be embodied in various forms without being limited to the exemplary embodiments set forth herein. Descriptions of well-known parts are omitted for clarity.

FIG. 1 is a lateral view of a fusion apparatus for fusing two vertebrae according to an exemplary embodiment. The apparatus according to an exemplary embodiment may include a plate 100, screws 110 and 120, and graft 130. The apparatus may be used to fuse vertebrae 140 and 150 by securing graft 130 in the disc space between vertebrae 140 and 150.

After the disc is removed from the disc space, a reamer may be used to carve out a channel between the vertebrae 140 and 150. Graft 130 may then be inserted into the carved channel between the vertebrae 140 and 150. Plate 100 is then secured to vertebrae 140 and 150 using screws 110 and 120. Plate 100 may cover an anterior gap between vertebrae 140 and 150, such that a first portion of plate 100 is disposed within the channel between vertebrae 140 and 150, and a second portion of plate 100 is disposed beyond an anterior surface 160 of the vertebrae 140 and 150. More specifically, plate 100 may extend in an anterior direction beyond the anterior surface 160 of vertebrae 140 and 150 by up to approximately 3 mm. Plate 100 may also be disposed at least 5 mm from an adjacent disc space. For example, plate 100 may be at least 5 mm from the disc space (not shown) above vertebrate 140. Plate 100 may also be at least 5 mm from both disc spaces that are adjacent to disc space 130. In other words, plate 100 may be at least 5 mm from the disc space above vertebrate 140, and at least 5 mm from the disc space below vertebrate 150.

By disposing the plate 100 on the anterior surface 160 of vertebrae 140 and 150, as opposed to within the disc space between vertebrae 140 and 150, the surface area of graft 130 is maximized, thus increasing the fusion rate. For example, the graft 130 may extend approximately 11 mm to 14 mm in a posterior direction from the anterior surface 160 of vertebrae 140 and 150. In addition, by disposing the plate 100 partially within the channel between vertebrae 140 and 150, as opposed to entirely on the anterior surface 160, a shorter plate 100 may be used in order to increase the distance between the plate 100 and adjacent discs. The increased distance to the adjacent discs may reduce the risk of damaging the adjacent discs.

Moreover, by disposing the plate 100 on the anterior surface 160 of the vertebrae 140 and 150, screws 110 and 120 are able to be inserted in a more anterior-posterior direction, as compared to zero-profile plates, which require that screws are inserted in a more cephalo-caudal direction. As shown in FIG. 1, each screw 110, 120 is insertable through a corresponding bore defined through plate 100. Each bore extends through an anterior portion 101 and a posterior portion 102 (FIG. 7A) of plate 100. In particular, a majority of an outer diameter of each bore extends through a thickness of anterior portion 101 and a thickness of posterior portion 102. Inserting the screws in a more anterior-posterior direction makes it easier for the surgeon to insert the screws. On the other hand, plates disposed entirely on the anterior surface of the vertebrae are affixed using screws inserted in the anterior-posterior direction. Inserting the screws at an angle, as shown in the exemplary embodiment of FIG. 1, may reduce the possibility that the screws will pull out of the vertebrae.

Figure 2:
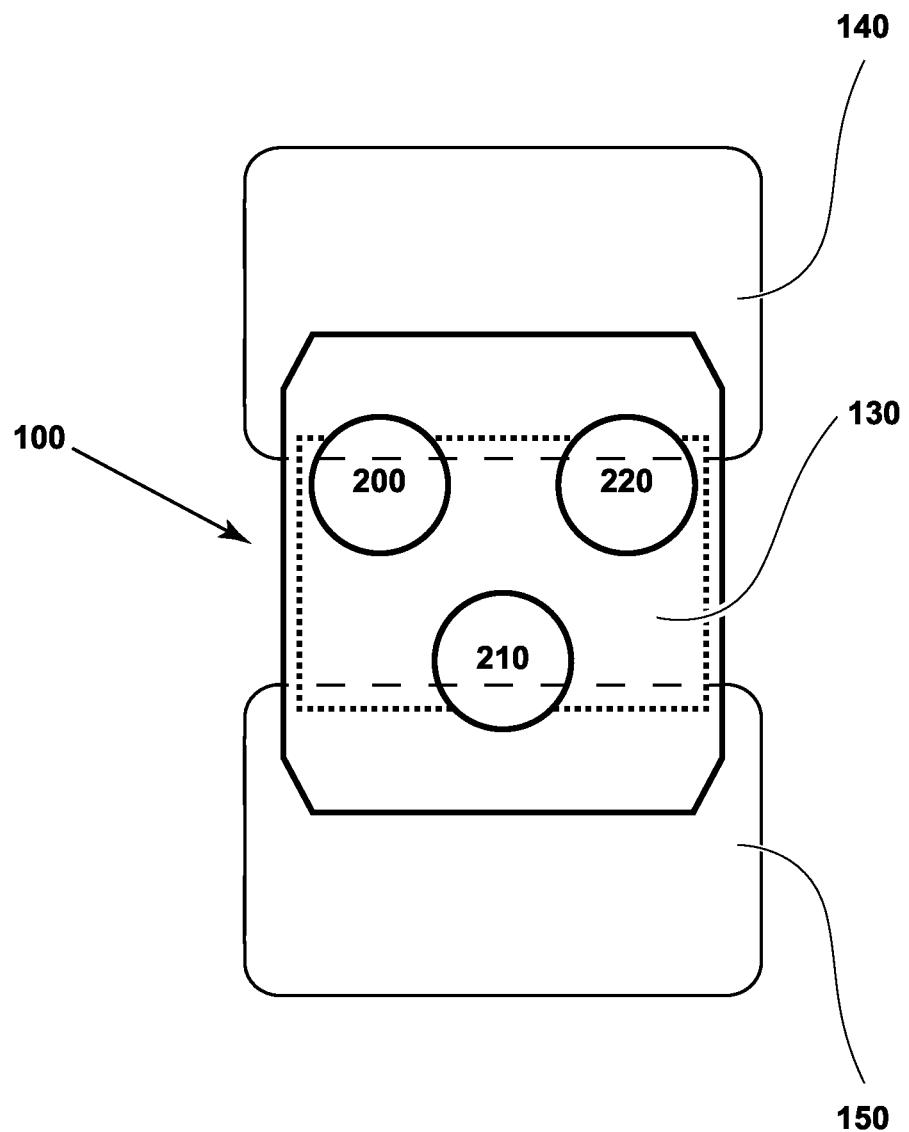
FIG. 2 is an anterior view of a fusion apparatus according to an exemplary embodiment.

FIG. 2 is an anterior view of a fusion apparatus for fusing two vertebrae according to an exemplary embodiment. In the exemplary embodiment of FIG. 2, three screws 200, 210, and 220 may be used to secure plate 100 to vertebrae 140 and 150. As shown in FIG. 2, each screw 200, 210, 220 is insertable through a corresponding bore defined through plate 100. Each bore extends through an anterior portion 101 and a posterior portion 102 (FIG. 7A) of plate 100. In particular, a majority of an outer diameter of each bore extends through a thickness of anterior portion 101 and a thickness of posterior portion 102. Screws 200 and 220 may screw into vertebrate 140 and screw 210 may screw into vertebrate 150. Screw 210 may be located between screws 200 and 220. Alternatively, according to another exemplary embodiment, a fourth screw (not shown) may be used to secure plate 100 to vertebrae 140 and 150. The fourth screw may be disposed such that two screws extend into vertebrate 140 and two screws extend into vertebrate 150. Of course, the ordinarily skilled artisan will appreciate from the instant disclosure that any number of screws in either or both of vertebrae 140 and 150 can be used without departing from the spirit and scope of the present teachings.

Figure 3:
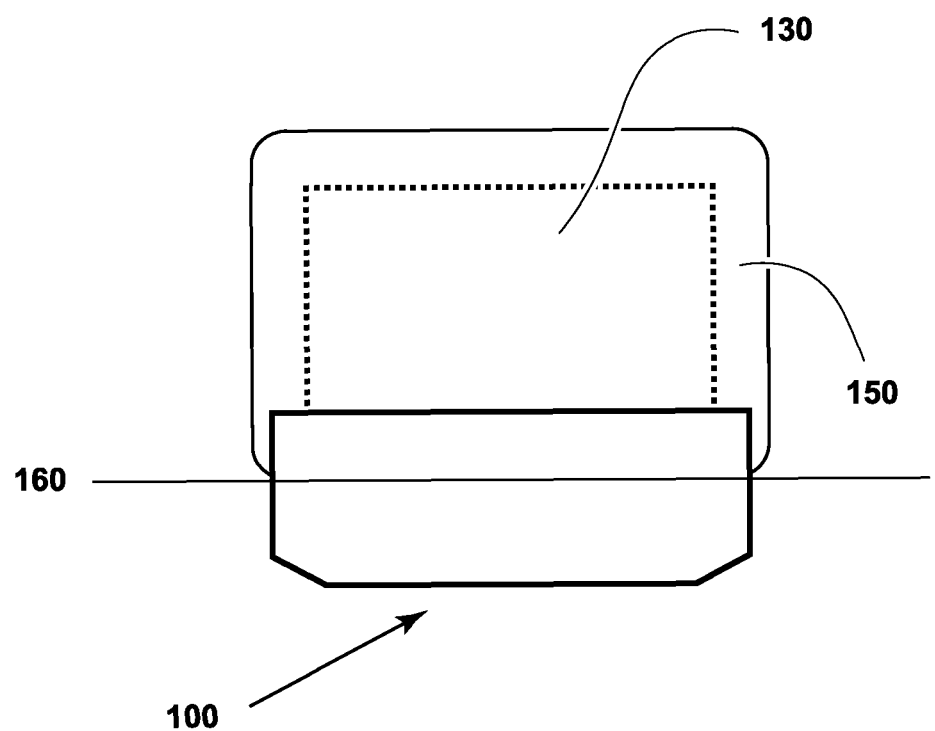
FIG. 3 is a cross-sectional view from the top of the spine of a fusion apparatus according to an exemplary embodiment.

FIG. 3 is a cross-sectional view of a fusion apparatus for fusing two vertebrae according to an exemplary embodiment. In the exemplary embodiment of FIG. 3, plate 100 may extend in the anterior direction beyond the anterior surface 160 of vertebrae 150. The plate 100 may also extend into the disc space where graft 130 is located. Graft 130 may extend in the posterior direction from plate 100 to substantially fill the remaining disc space. For example, graft 130 may extend approximately 11 mm to approximately 14 mm in the posterior direction. By allowing part of plate 100 to protrude from the anterior surface of the vertebrae, the surface area of the graft 130 may be increased.

Figure 4:
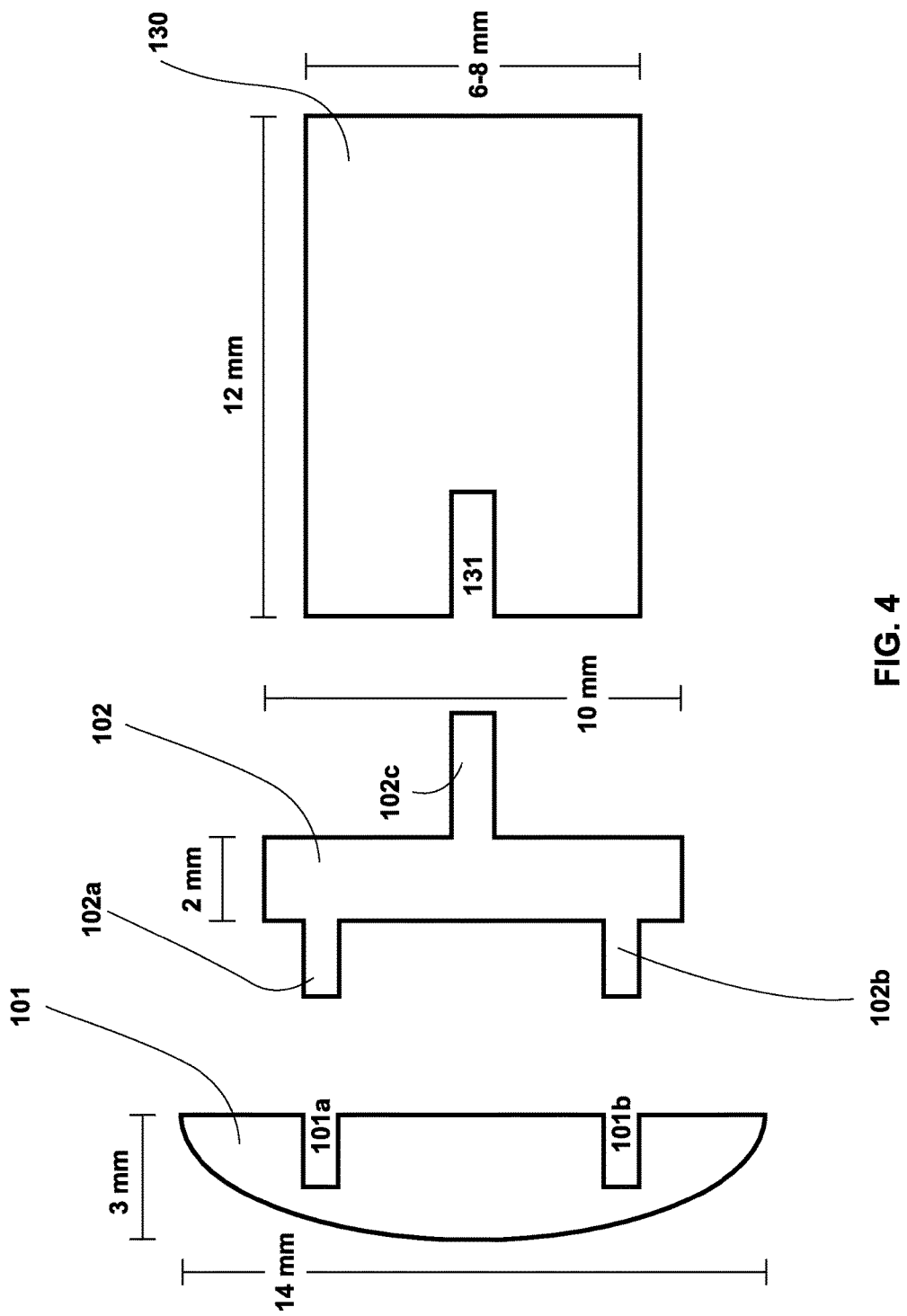
FIG. 4 is an exploded view of a fusion apparatus according to an exemplary embodiment.

FIG. 4 is an exploded view of a fusion apparatus for fusing two vertebrae according to an exemplary embodiment. In the exemplary embodiment of FIG. 4, the plate may include an anterior portion 101 and a posterior portion 102. Anterior portion 101 may include a first recess 101a and a second recess 101b. Posterior portion 102 may include a first protrusion 102a, a second protrusion 102b, and a third protrusion 102c. First protrusion 102a and second protrusion 102b may extend in the anterior direction toward the anterior portion 101 of plate 100. First recess 101a and second recess 101b may receive first protrusion 102a and second protrusion 102b, respectively. First protrusion 102a and second protrusion 102b may be hollow in order to receive screws that affix the plate 100 to vertebrae 140 and 150. Third protrusion 102c may extend in the posterior direction toward the graft 130, which may include a graft recess 131 to receive the third protrusion 102c. The third protrusion 102c may be in the form of an arrowhead or other shape that connects the posterior portion 102 to graft 130. Alternatively, posterior portion 102 may not include a third protrusion 102c, and graft 130 may not include graft recess 131, so that plate 100 is not affixed to graft 130. In addition, anterior portion 101 and posterior portion 102 may be integral such that they form one solid plate.

According to an exemplary embodiment, anterior portion 101 may be approximately 14 mm long in the cephalo-caudal direction and approximately 3 mm deep in the anterior-posterior direction. Posterior portion 102 may be approximately 10 mm long in the cephalo-caudal direction and approximately 2 mm deep in the anterior-posterior direction. Graft 130 may be approximately 6 mm to 8 mm long in the cephalo-caudal direction, and approximately 12 mm deep in the anterior-posterior direction.

According to an exemplary embodiment, anterior portion 101 may be made of titanium or another metallic material. Posterior portion 102 may be made of polyether ether ketone (PEEK) or another non-metal material. Alternatively, according to another exemplary embodiment, anterior portion 101 may be made of PEEK or another non-metal material, and posterior portion 102 may be made of titanium or another metallic material. According to yet another exemplary embodiment, anterior portion 101 and posterior portion 102 may be made of titanium or another metallic material. Graft 130 may be made of bone, which may come from the patient or may be a cadaveric bone. Graft 130 may also be made of man-made plastic or ceramic material that may be packed with living bone tissue taken from the patient's spine during surgery.

Figure 5:
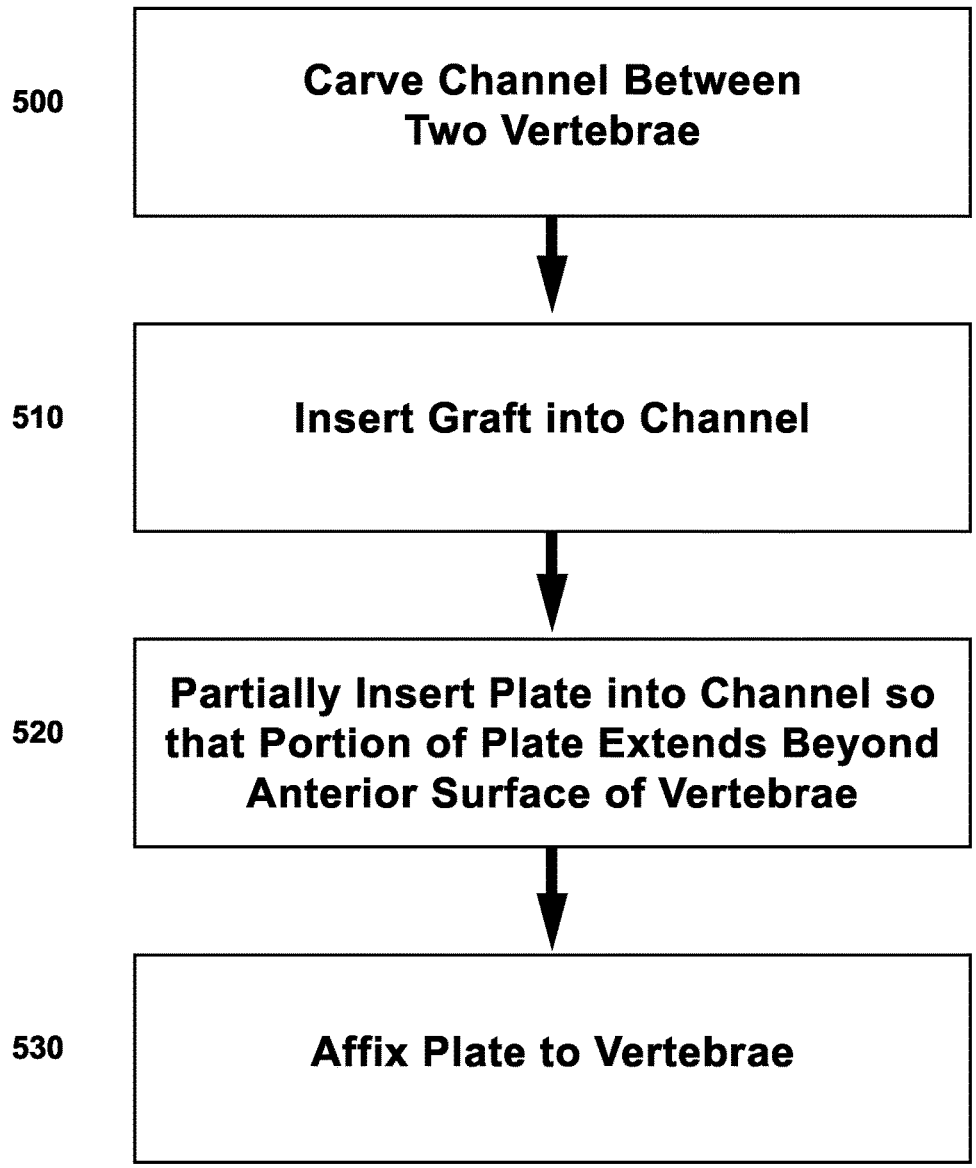
FIG. 5 is a flowchart of a method for fusing two vertebrae according to an exemplary embodiment.

FIG. 5 is a flowchart of a method for fusing two vertebrae according to an exemplary embodiment. FIG. 6 is a side view of a reamer that may be used in the method of FIG. 5. Referring to FIG. 5, the method of the exemplary embodiment begins at step 500 in which a channel is carved between two vertebrae. The reamer shown in FIG. 6 may be used to perform the carving step 500 of FIG. 5.

Referring to FIG. 6, reamer 600 may include a posterior portion 610 and an anterior portion 620. According to an exemplary embodiment, the cephalo-caudal height of the anterior portion 620 may be greater than the cephalo-caudal height of the posterior portion 610. For example, the anterior portion 620 may be approximately 10 mm long in the cephalo-caudal direction, and posterior portion 610 may be approximately 6 mm to approximately 8 mm long in the cephalo-caudal direction. In addition, anterior portion 620 may have a shorter anterior-posterior depth as compared to the anterior-posterior depth of posterior portion 610. For example, anterior portion 620 may have a depth of approximately 2 mm, and posterior portion 610 may have a depth of approximately 12 mm.

As the reamer 600 is inserted between vertebrae 140 and 150, the posterior portion 610 carves out a channel between the vertebrae 140 and 150. As the reamer 600 is inserted further, anterior portion 620 carves out a wider channel, such that a posterior end of the channel has a smaller cephalo-caudal height than an anterior end of the channel.

The dimensions of the reamer 600, and the other components, described herein are merely exemplary, and may vary. For example, the cephalo-caudal height of posterior portion 610 and anterior portion 620 may be set to correspond to the size of the graft and the size of the plate, respectively, to be inserted in the channel created by reamer 600. The cephalo-caudal height of posterior portion 610 and the cephalo-caudal height of the graft may vary, for example, in 1 mm or 0.5 mm increments. In addition, the cephalo-caudal height of the anterior portion 610 and the cephalo-caudal height of the plate may vary, for example, in 1 mm or 0.5 mm increments. According to an exemplary embodiment, the cephalo-caudal height of the anterior portion 610 and the cephalo-caudal height of the plate may be selected so that the plate is partially recessed into the anterior end of the channel when the plate is affixed to the vertebrae.

Referring to FIG. 5, in step 510, a graft is inserted into the channel carved in step 500. Graft 130 may be made of bone, which may come from the patient or may be a cadaveric bone. Graft 130 may also be made of man-made plastic or ceramic material that may be packed with living bone tissue taken from the patient's spine during surgery.

In step 520, a plate is partially inserted into the channel carved in step 500, so that a portion of the plate extends in the anterior direction beyond the anterior surface of the vertebrae. For example, the plate may extend approximately 2 mm into the channel, and may extend approximately 3 mm in the anterior direction beyond the anterior surface of the vertebrae.

In step 530, the plate is affixed to the vertebrae using two or more screws. According to an exemplary embodiment, three screws may be used to affix the plate, with first and second screws being screwed into the top vertebrate, and a third screw screwed into the bottom vertebrate. In this exemplary configuration, the third screw may be disposed horizontally (i.e., left-right on the patient's body) between the first and second screws. Alternatively, the first and second screws may be screwed into the bottom vertebrate, and the third screw may be screwed into the top vertebrate. In this exemplary configuration, the third screw may be disposed horizontally between the first and second screws. According to yet another embodiment, four screws may be used to affix the plate to the vertebrae in step 530. In this exemplary configuration, two screws may be screwed into each of the top vertebrate and bottom vertebrate. According to still another exemplary embodiment, two screws may be used to affix the plate to the vertebrae, with one screw being screwed into each of the top vertebrate and bottom vertebrate.

Figure 7A:
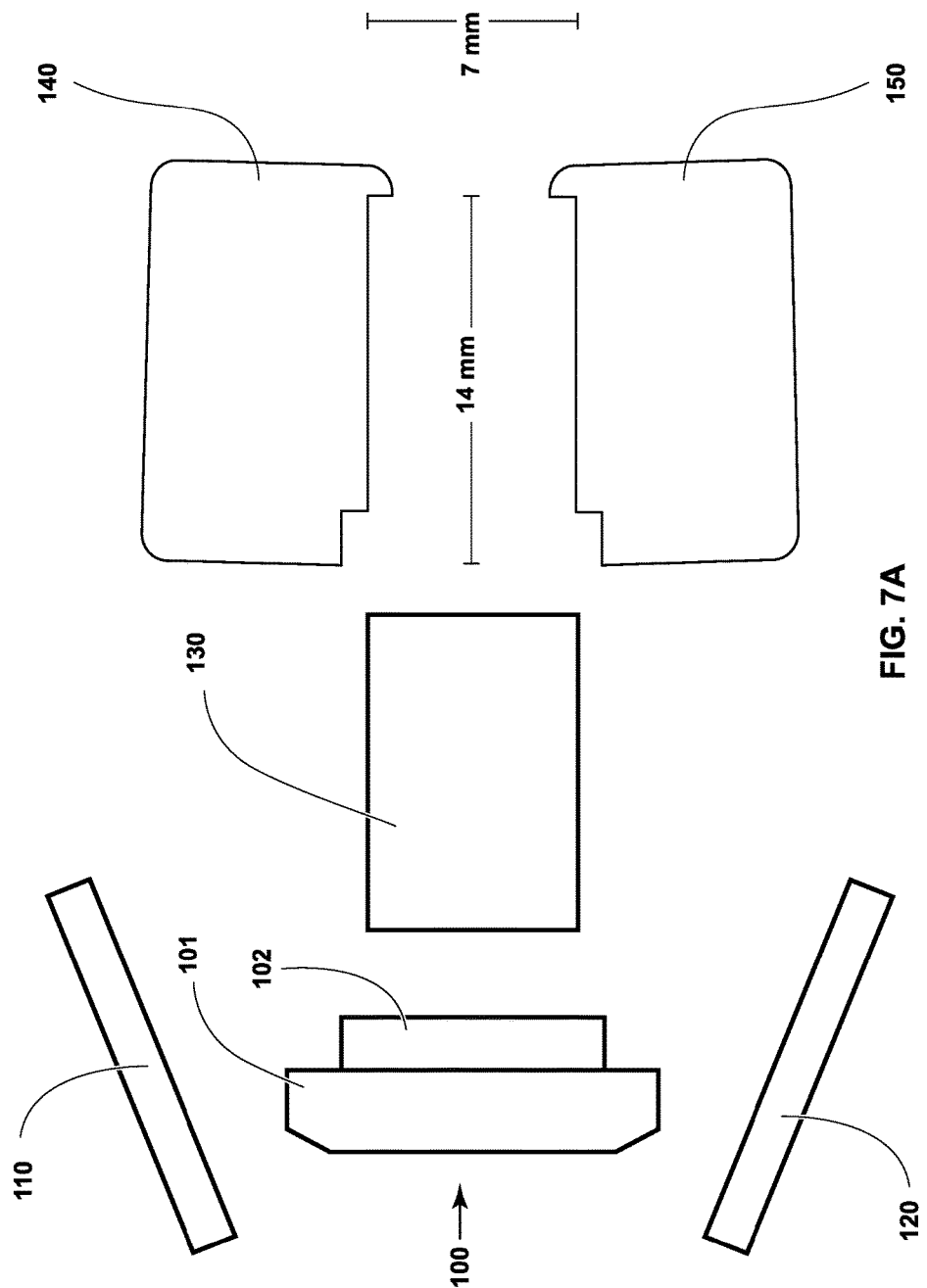

FIGS. 7A through 7E illustrate exploded views of the apparatus according to an exemplary embodiment as the apparatus is affixed to the vertebrae. Referring to FIG. 7A, a channel has been carved between vertebrae 140 and 150. The channel may have a major diameter to accommodate plate 100 and a minor diameter to accommodate graft 130. According to an exemplary embodiment, the minor diameter may be 7 mm in the cephalo-caudal direction, and the major diameter may be approximately 10 mm in the cephalo-caudal direction. The channel may have a depth of 14 mm in the anterior-posterior direction. In the exemplary embodiment, plate 100 may be a solid component including an anterior portion 101 and a posterior portion 102. The cephalo-caudal height of anterior portion 101 may be greater than the cephalo-caudal height of posterior portion 102.

In FIG. 7B, the graft 130 has been inserted into the minor diameter of the channel. The graft 130 may extend from an anterior end of the minor-diameter channel to a posterior end of the minor-diameter channel.

Figure 7C:
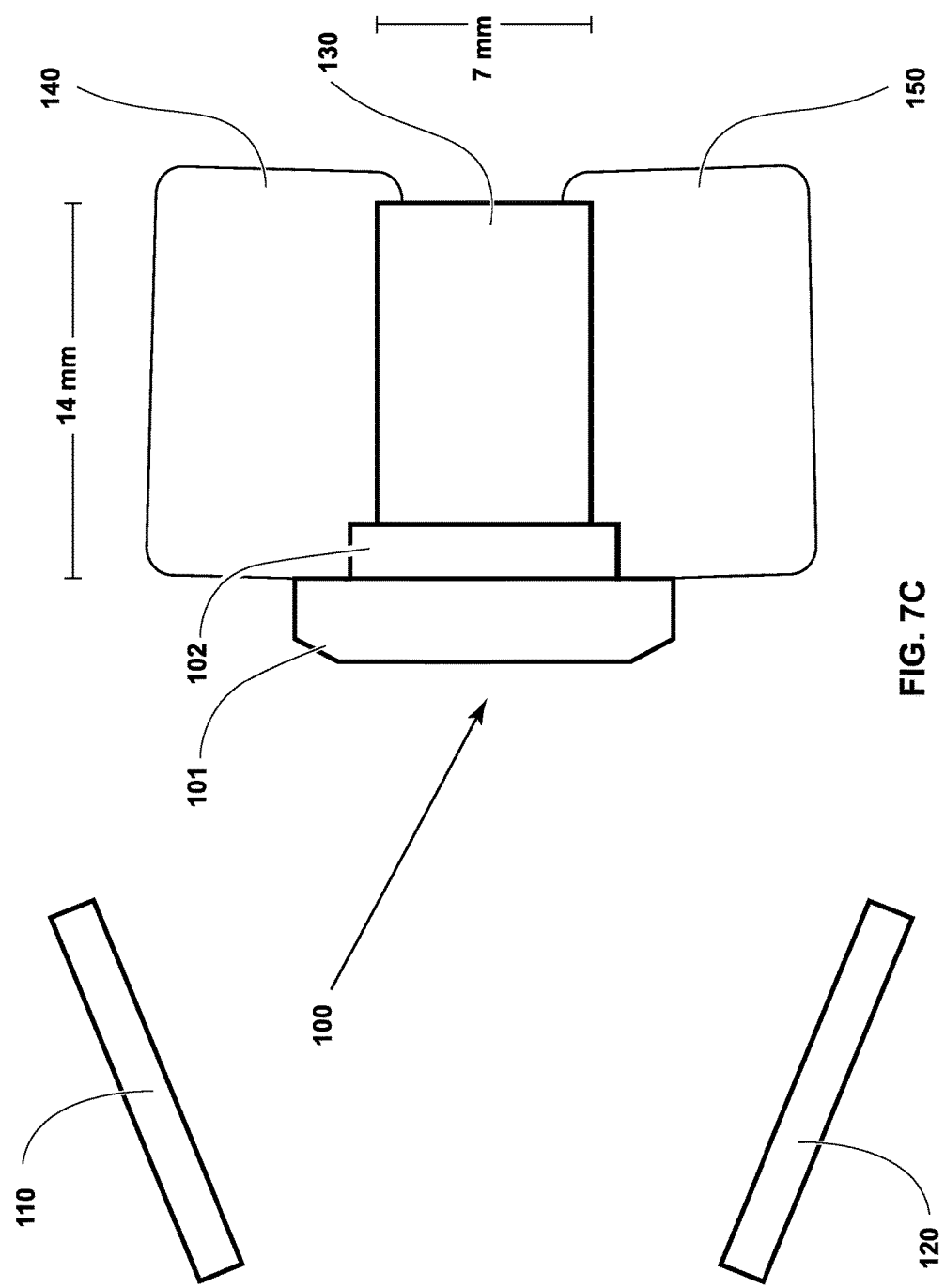

In FIG. 7C, plate 100 has been disposed so that the posterior portion 102 fits within the major-diameter portion of the channel and the anterior portion 101 resides on the anterior surface of vertebrae 140 and 150. Posterior portion 102 may abut the anterior end of graft 130.

Figure 7D:
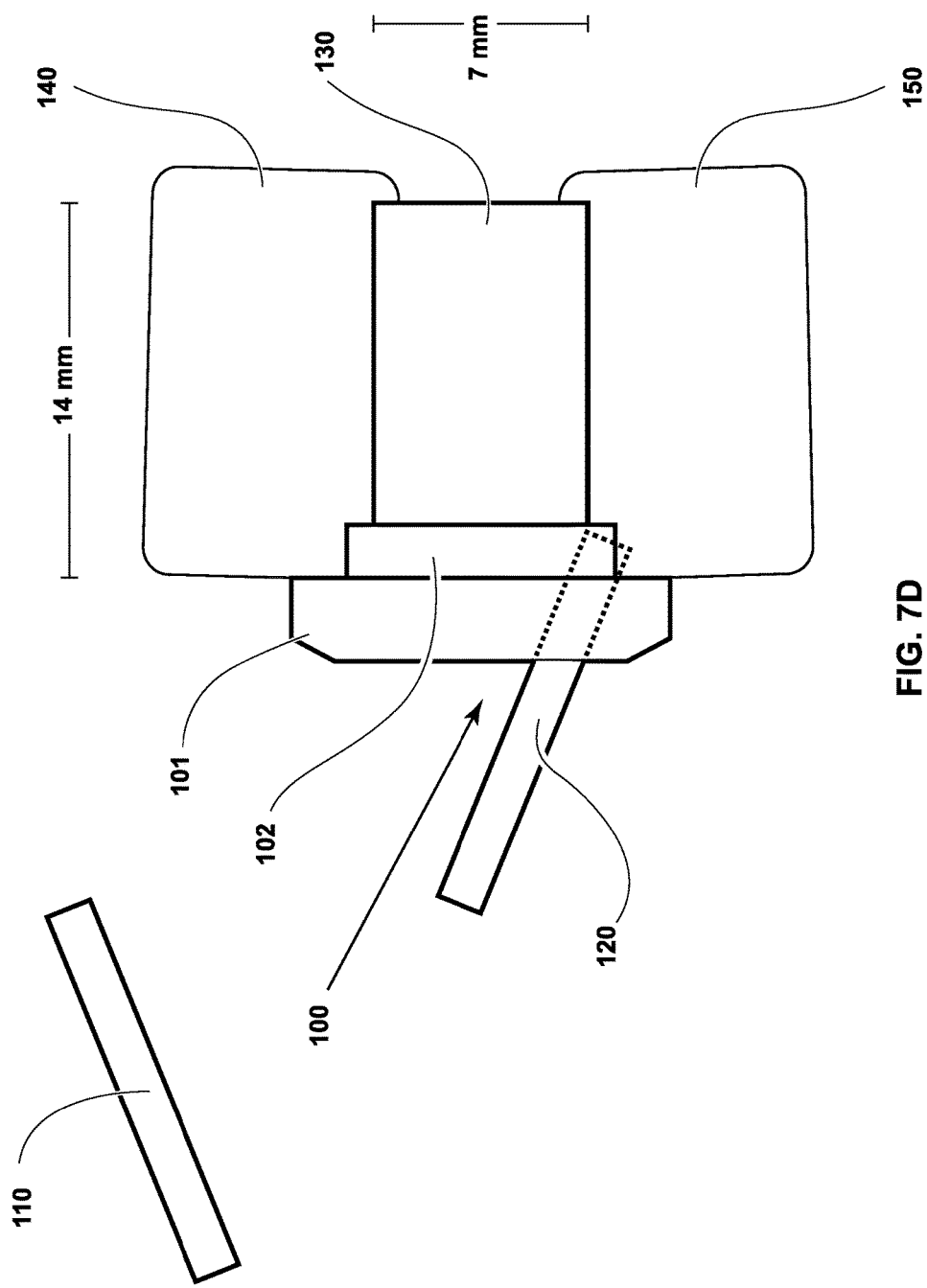

In FIG. 7D, screw 120 is positioned so as to be inserted through plate 100 into vertebrate 150. Screw 120 may be inserted into vertebrate 150 at an angle between the cephalo-caudal direction and the anterior-posterior direction. Because anterior portion 101 of plate 100 is located on the anterior surface of vertebrae 140 and 150, screw 120 is easier to insert, as compared with inserting a screw into a plate that is disposed entirely within the space between vertebrae 140 and 150. In addition, because the posterior portion 102 is disposed within the channel between vertebrae 140 and 150, plate 100 may have a lesser cephalo-caudal height as compared to a plate disposed entirely on the anterior surface of vertebrae 140 and 150. The configuration shown in FIG. 7D allows for angled screw insertion, which reduces the possibility that the screw 120 will pullout as compared to screws inserted in the anterior-posterior direction.

Figure 7E:
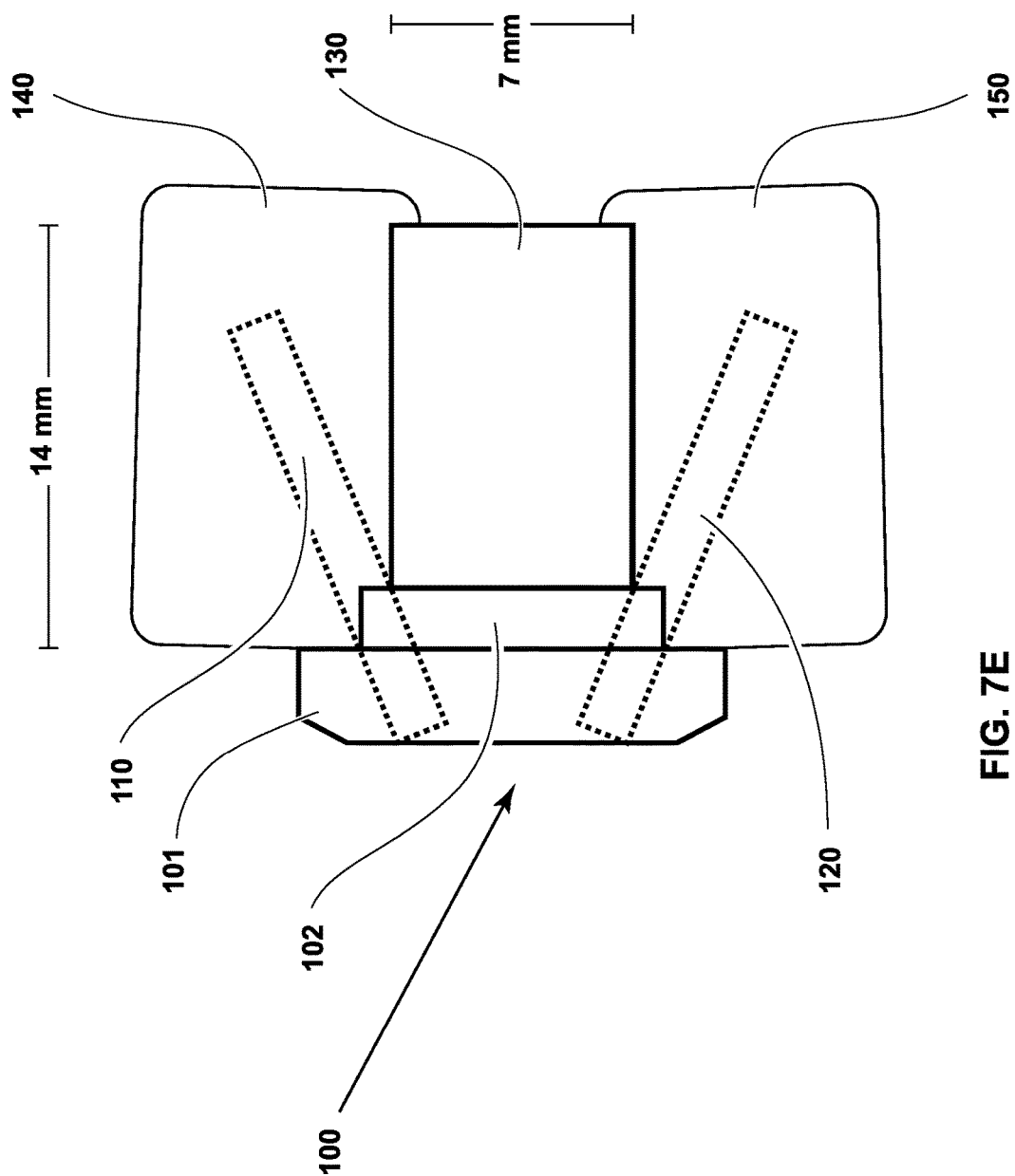

In FIG. 7E, both screws 110 and 120 are inserted at an angle into vertebrae 140 and 150, respectively. Each screw 110, 120 is insertable through a corresponding bore defined through plate 100, as described in detail hereinabove. Although only two screws are shown in FIGS. 7A-7E, one of ordinary skill in the art would understand that additional screws may be used.

Figure 8A:
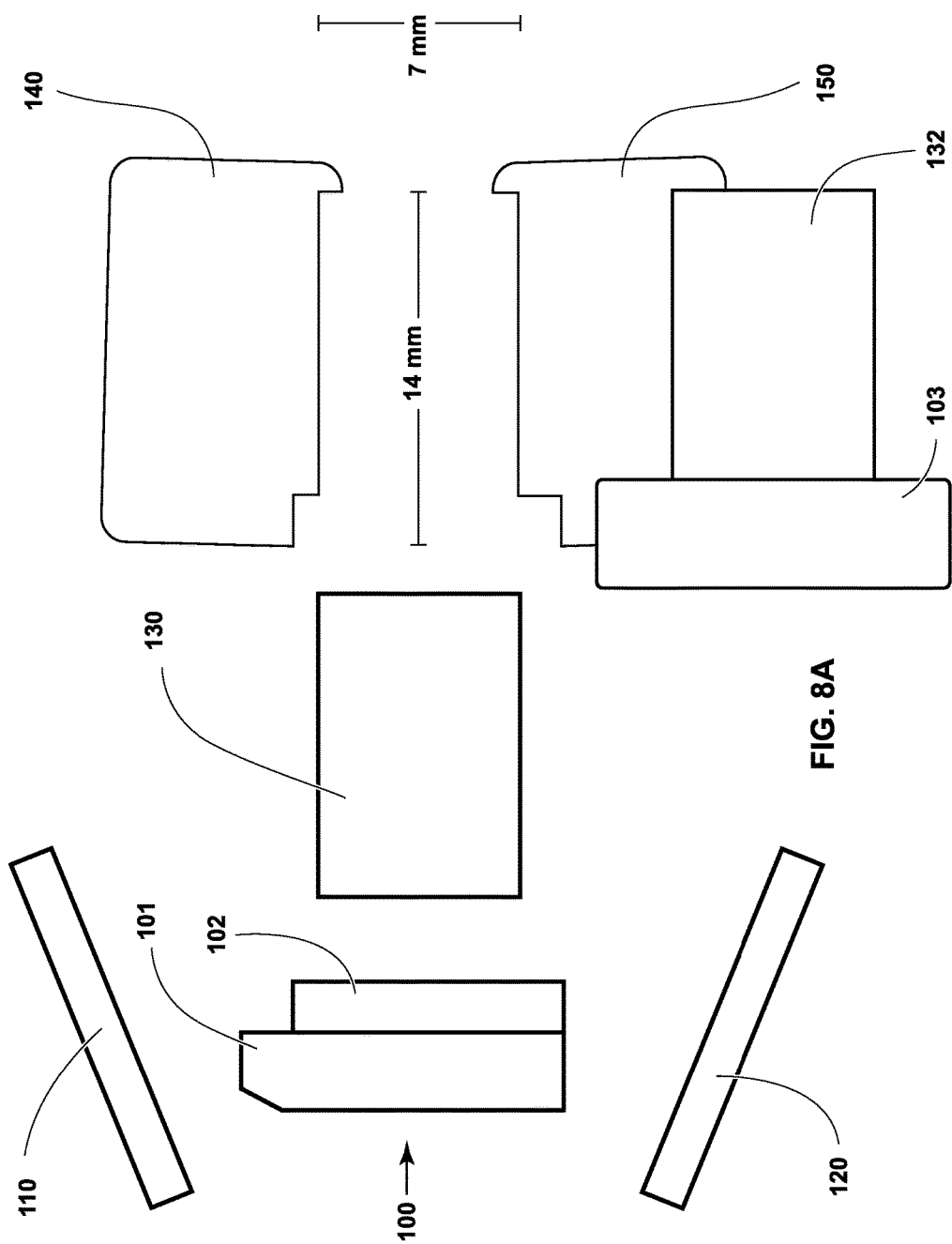

FIGS. 8A through 8E illustrate exploded views of the apparatus according to another exemplary embodiment as the apparatus is affixed to the vertebrae. Referring to FIG. 8A, a pre-existing plate 103 has been previously affixed to vertebrate 150 in order to secure bone graft 132 within the disc space below vertebrate 150 in the caudal direction. Because of the close proximity of pre-existing plate 103 to the channel between vertebrate 140 and 150, it may not be possible to use the plate 100 shown in FIGS. 7A-7E because plate 100 and pre-existing plate 103 may interfere with each other. However, in certain cases of revision, add-on, or adjacent segment disease (ASD, also called adjacent segment pathology, ASP), it may be beneficial to not remove pre-existing plate 103. A zero-profile plate could be used in order to avoid interfering with pre-existing plate 103, however, zero-profile plates may not achieve proper fusion in this case.

Figure 8C:
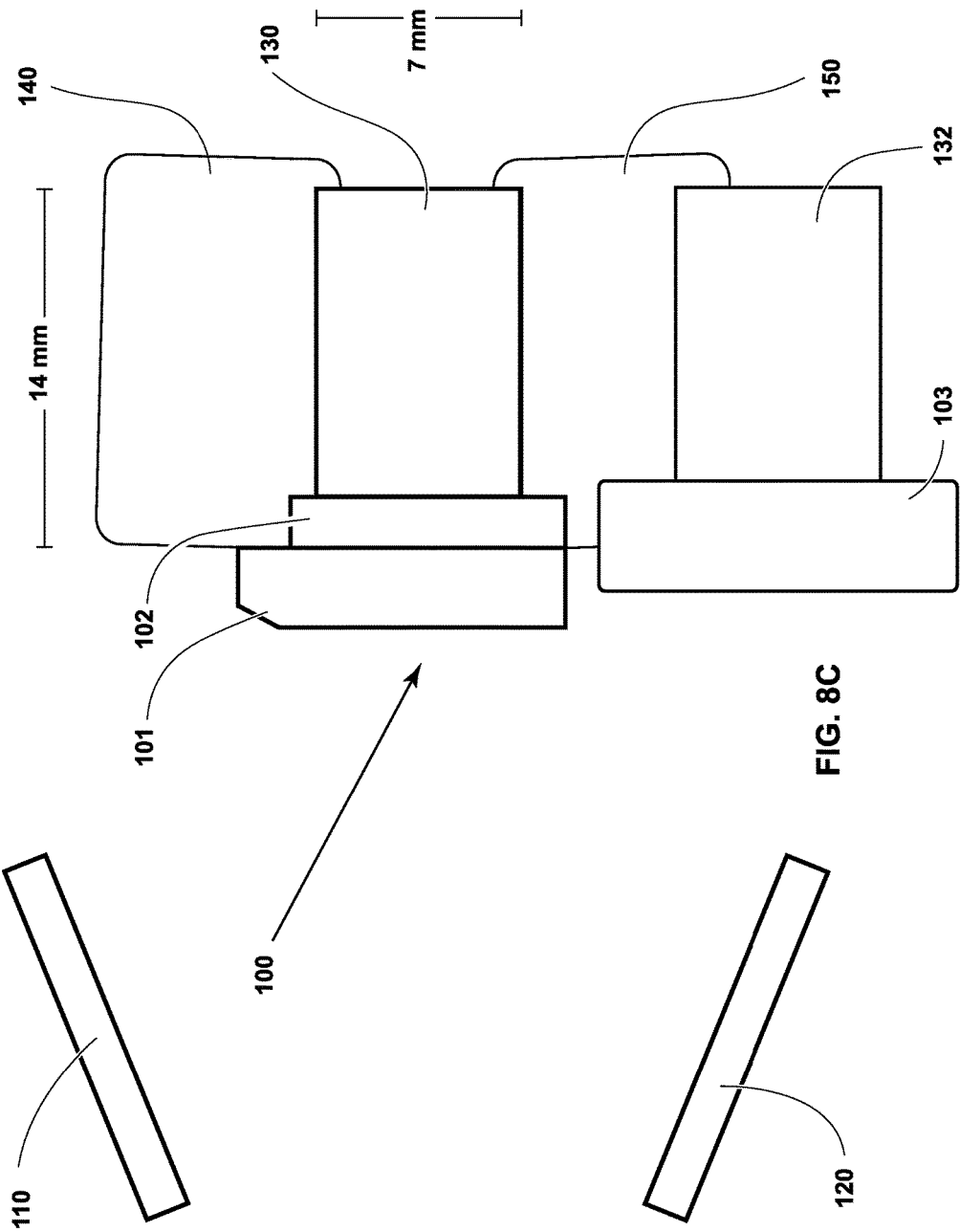

Accordingly, as shown in FIG. 8A, a modified version of plate 100 may be used in which an anterior portion of the plate does not extend beyond the major diameter of the channel in the cephalo-caudal direction. As shown in FIGS. 8B and 8C, graft 130 is inserted into the channel between vertebrae 140 and 150. More specifically, graft 130 is inserted into the minor diameter or posterior portion of the channel. In FIG. 8C, plate 100 is inserted into the major diameter or anterior portion of the channel such that a cephalad end of the plate 100 extends beyond the major diameter of the channel in the cephalad direction. The caudal end of plate 100 does not extend beyond the major diameter of the channel in order to avoid interfering with pre-existing plate 103.

Figure 8D:
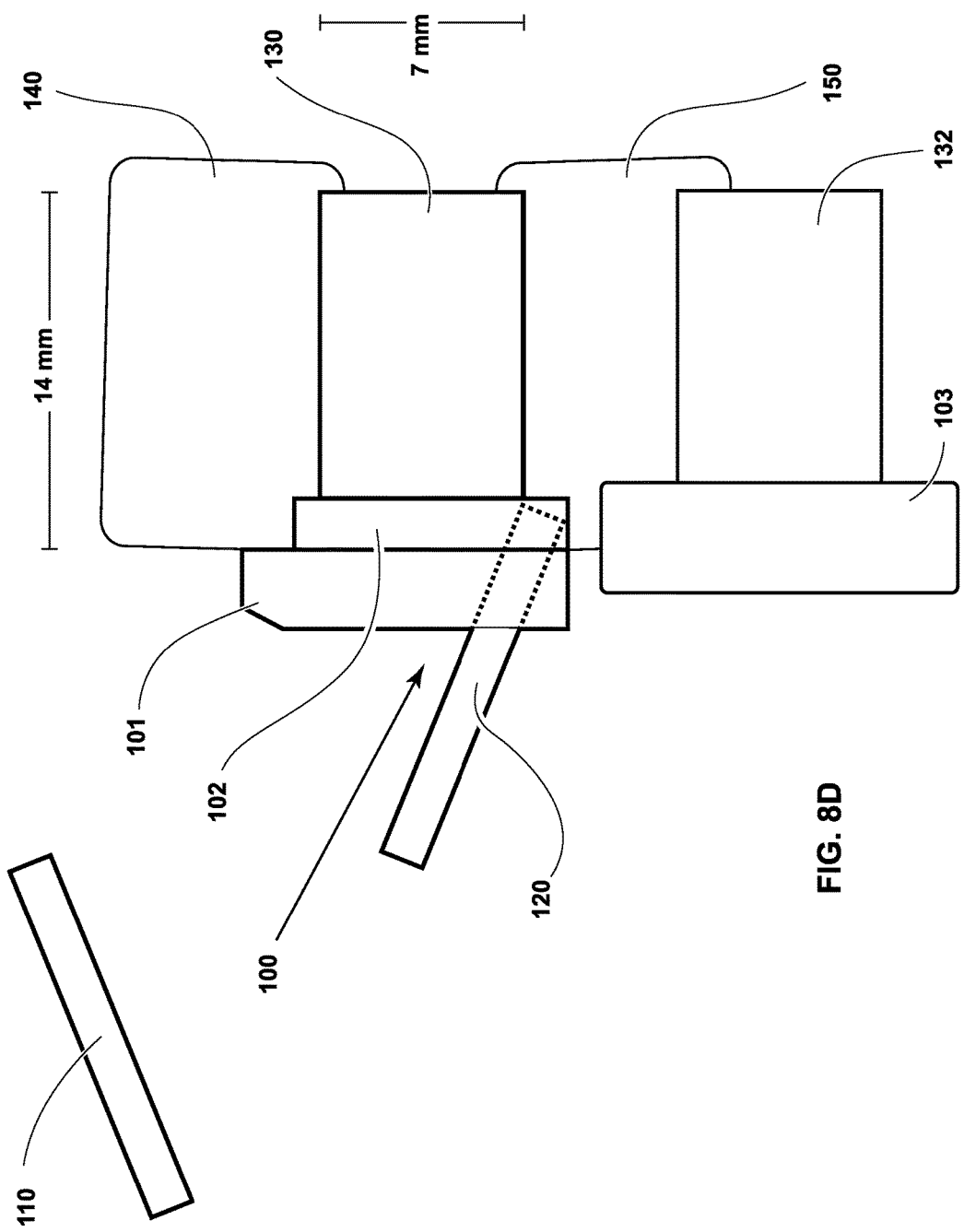
Figure 8E:
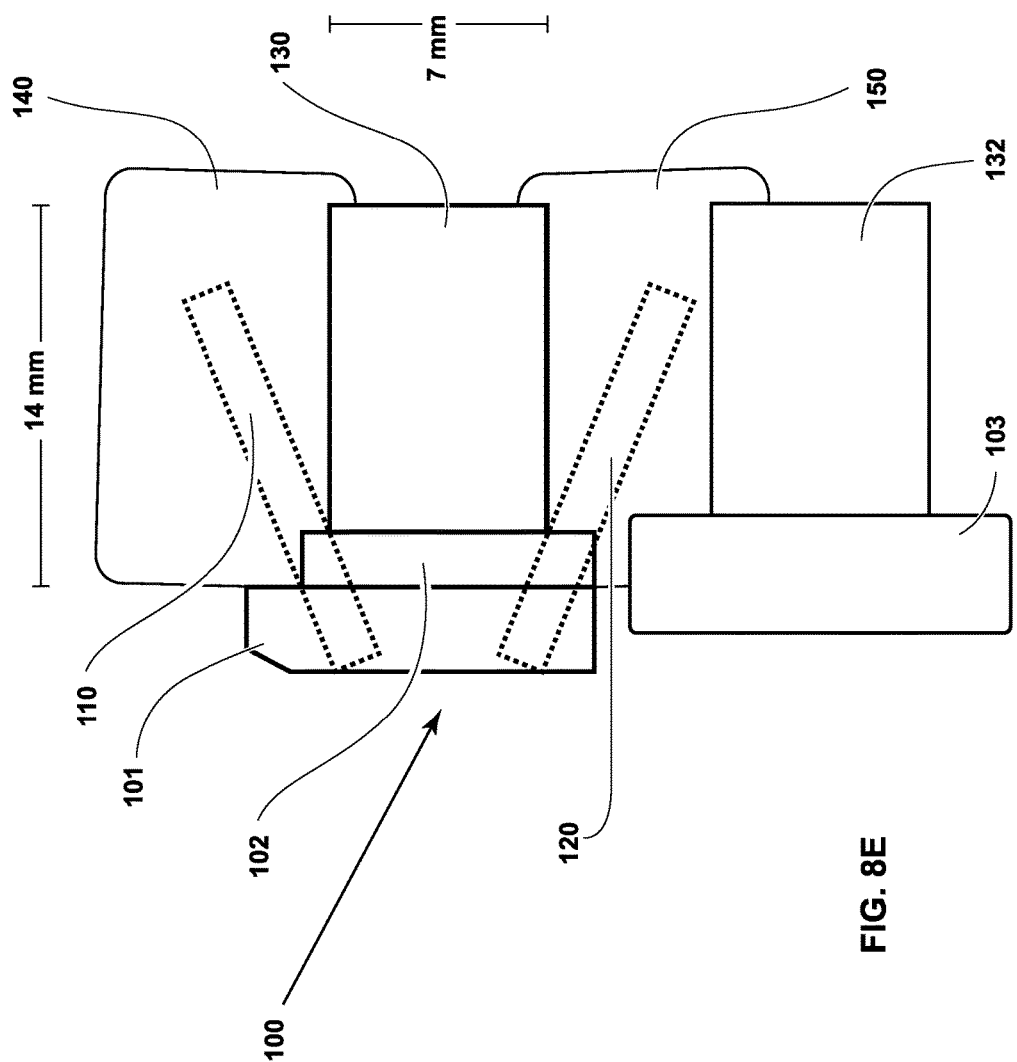

In FIG. 8D, screw 120 is positioned so as to be inserted through plate 100 into vertebrate 150. Screw 120 may be inserted near the caudal end of plate 100, which does not extend beyond the major diameter of the channel. In FIG. 8E, both screws 110 and 120 are inserted into vertebrate 140 and 150, respectively, to secure plate 100. Each screw 110, 120 is insertable through a corresponding bore defined through plate 100, as described in detail hereinabove.

Although a few exemplary embodiments of the present general inventive concept have been shown and described, it will be appreciated by those skilled in the art that changes may be made in these embodiments without departing from the principles and spirit of the general inventive concept, the scope of which is defined in the appended claims and their equivalents.

What is claimed is:

1. An apparatus comprising:
a plate configured to be affixed to at least two vertebrae, the plate including a flat anterior portion extending anteriorly from anterior surfaces of the at least two vertebrae without extending posteriorly into a disc space between the at least two vertebrae, and a posterior portion detachably connected to the anterior portion, the anterior portion includes two recesses and the posterior portion includes two hollow anterior protrusions, the two recesses of the anterior portion are configured to receive the two hollow anterior protrusions of the posterior portion, the anterior and posterior portions oriented in a cephalo-caudad direction and the anterior portion has a length greater than a length of the posterior portion in the cephalo-caudad direction; and
at least two screws configured to affix the plate to the at least two vertebrae;
a graft having a recess;
wherein the plate has dimensions such that, when the plate is affixed to the at least two vertebrae, the plate is partially disposed in a disc space between the at least two vertebrae, and extends in an anterior direction beyond the anterior surfaces of the at least two vertebrae;
wherein the anterior portion extends in an anterior direction beyond the anterior surfaces of the at least two vertebrae and the posterior portion is configured to be detachably connected to the graft disposed between the at least two vertebrae; and
wherein the posterior portion includes a posterior protrusion configured to extend into the recess of the graft disposed between the at least two vertebrae.

2. The apparatus of claim 1, wherein the plate has dimensions such that when the plate is affixed to the at least two vertebrae, the plate extends no more than 3 mm in the anterior direction beyond the anterior surfaces of the at least two vertebrae.

3. The apparatus of claim 1, wherein the plate comprises two cephalo-caudal ends; and
wherein the plate has dimensions such that, when the plate is affixed to the at least two vertebrae, a first cephalo-caudal end of the plate is located at least 5 mm from a disc nearest to the first cephalo-caudal end in a cephalo-caudal direction.

4. The apparatus of claim 3, wherein the plate has dimensions such that, when the plate is affixed to the at least two vertebrae, a second cephalo-caudal end of the plate is located at least 5 mm from a disc closest to the second cephalo-caudal end in the cephalo-caudal direction.

5. The apparatus of claim 1, wherein the graft is configured to be disposed between the at least two vertebrae; and wherein the graft has dimensions such that, when the graft is placed within the disc space, the graft extends approximately 11 mm to 14 mm in a posterior direction from the anterior surfaces of the at least two vertebrae.

6. The apparatus of claim 1, wherein the plate extends approximately 14 mm in a cephalo-caudal direction that is parallel to the anterior surfaces of the at least two vertebrae.

7. The apparatus of claim 1, wherein the anterior portion is made of titanium or other metal and the posterior portion is made of polyetheretherketone (PEEK) or other non-metallic substance.

8. The apparatus of claim 1, wherein the graft is configured to be disposed between the at least two vertebrae;
wherein the posterior portion of the plate has a thickness of approximately 2 mm such that it extends approximately 2 mm in a posterior direction from the anterior surfaces of the at least two vertebrae; and
wherein the graft is configured to extend approximately 12 mm in a posterior direction from the posterior portion of the plate.

9. The apparatus of claim 1, wherein the at least two screws comprise:
first and second screws configured to extend into a top vertebra of the at least two vertebrae; and
a third screw configured to be disposed between the first and second screws, and configured to extend into a bottom vertebra of the at least two vertebrae.

10. The apparatus of claim 1, wherein a thickness of the plate, as measured in an anterior-posterior direction, does not exceed 5 mm.

11. The apparatus of claim 10, wherein the plate comprises:
the posterior portion dimensioned to extend into the disc space by no more than 2 mm, and
the anterior portion dimensioned such that it cannot extend into the disc space.

12. The apparatus of claim 1, wherein the ratio of a distance that the plate extends into the disc space to a distance the plate extends in the anterior direction is 1.

13. An apparatus comprising:
a plate for attachment to at least two vertebrae, the plate comprising a flat anterior portion extending anteriorly from anterior surfaces of the at least two vertebrae without extending posteriorly into the disc space between the at least two vertebrae, the anterior portion having a length greater than a height of the disc space, and a flat posterior portion extending posteriorly into the disc space from the anterior surfaces of the at least two vertebrae without extending anteriorly out of the disc space, the anterior and posterior portions oriented in a cephalo-caudad direction and the anterior portion has a length greater than a length of the posterior portion in the cephalo-caudad direction;
a graft disposed posteriorly of the posterior portion;
at least two bores defined through the anterior portion and the posterior portion, a majority of an outer diameter of each bore extending through a thickness of the anterior portion and a thickness of the posterior portion;
at least two screws to attach the plate to the at least two vertebrae, the at least two screws insertable through the at least two bores defined through the anterior portion and the posterior portion, the at least two screws including:
first and second screws configured to extend into a top vertebra of the at least two vertebrae, and
a third screw configured to be disposed between the first and second screws, and configured to extend into a bottom vertebra of the at least two vertebrae.

14. The apparatus of claim 13, wherein a thickness of the anterior portion of the plate is less than 3 mm and a thickness of the posterior portion of the plate is less than 2 mm.

15. The apparatus of claim 13, wherein the ratio of a thickness of the posterior portion of the plate to a thickness of the anterior portion of the plate is 1 or less.

\* \* \* \* \*